United States Patent [19]
Pang et al.

[11] Patent Number: 5,137,878
[45] Date of Patent: Aug. 11, 1992

[54] COMPOSITION AND METHOD FOR TREATMENT OF SENILE DEMENTIA

[76] Inventors: Peter K. T. Pang, 52225 Range Road, 205 Carriage Lane, Sherwood Park, Alberta, Canada, T8A 2A6; Lawrence C. H. Wang, 406 Rooney Crescent, Edmonton, Alberta, Canada, T6R 1C8; Christina G. Benishin, 218-53431 Range Rd., 221, Ardressan, Alberta, Canada, T0B 0E0; Hsing J. Liu, 3543-105B St., Edmonton, Alberta, Canada, T6J 2K9

[21] Appl. No.: 768,423

[22] PCT Filed: Jan. 12, 1990

[86] PCT No.: PCT/US90/00/21

§ 371 Date: Sep. 13, 1991

§ 102(e) Date: Sep. 13, 1991

[87] PCT Pub. No.: WO90/08315

PCT Pub. Date: Jul. 26, 1990

Related U.S. Application Data

[63] Continuation-in-part of Ser. No. 297,021, Jan. 13, 1989, Pat. No. 4,966,893.

[51] Int. Cl.$^5$ .................. A61K 31/751; A01N 31/00; G01N 31/00
[52] U.S. Cl. .................. 514/54; 514/879; 424/195.1; 536/5; 536/127; 536/128
[58] Field of Search .............. 514/54, 879; 424/195.1; 536/5, 127, 128

[56] References Cited

U.S. PATENT DOCUMENTS

| | | | |
|---|---|---|---|
| 4,157,894 | 6/1979 | Bombardelli | 536/5 |
| 4,317,816 | 3/1982 | Arichi et al. | 514/26 |
| 4,339,442 | 7/1982 | Takemoto et al. | 536/5 |
| 4,446,130 | 5/1984 | Hachiya et al. | 424/195.1 |
| 4,621,137 | 11/1986 | Miyake et al. | 536/6.3 |
| 4,647,460 | 3/1987 | Lee | 424/195.1 |
| 4,684,628 | 8/1987 | Liu | 514/824 |
| 4,687,761 | 8/1987 | Liu | 514/26 |
| 4,755,504 | 7/1988 | Liu | 536/6.3 |
| 4,814,339 | 3/1989 | Rotondo | 514/332 |
| 4,837,219 | 6/1989 | Hutterer | 514/400 |
| 4,847,082 | 7/1989 | Sabin | 514/102 |
| 4,851,414 | 7/1989 | Shiozaki et al. | 514/277 |
| 4,966,893 | 10/1990 | Pang et al. | 514/54 |
| 5,071,839 | 12/1991 | Liu | 514/54 |

*Primary Examiner*—Ronald W. Griffin
*Attorney, Agent, or Firm*—Nikaido, Marmelstein, Murray & Oram

[57] ABSTRACT

Ginsenosides $Rb_1$ and $Rg_1$ enhance the availability of acetylcholine in the cortical and hippocampal regions of the brain and alleviaate the symptoms of Alzheimer-type senile dementia. The $Rb_1$ or $Rg_1$ may be administered together with a metabolic precursor for acetylcholine and/or with a cholinesterase inhibitor.

Pure $Rb_1$ is located from a mixture of ginsenosides by a process involving vacuum chromatography on silica gel. Preferably, the mixture of ginsenosides is enriched in $Rb_1$ by partition between an aqueous system and water ethyl acetatebutanol.

11 Claims, 15 Drawing Sheets

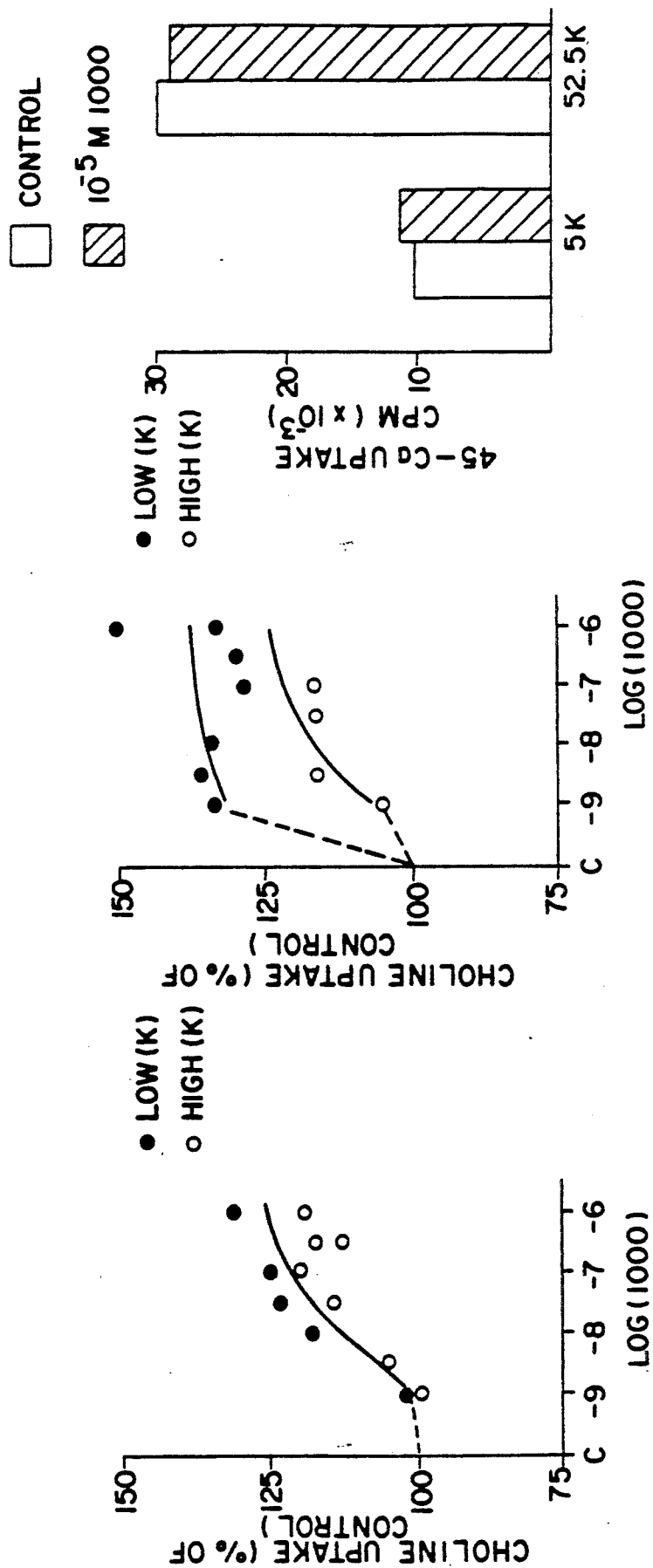

COMPOSITION AND METHOD FOR TREATMENT OF SENILE DEMENTIA

This application is a continuation-in-part of application Ser. No. 07/297,012, filed Jan. 13, 1989, now U.S. Pat. No. 4,966,893.

The present invention is directed to compositions, and methods for alleviating the symptoms of senile dementia of the Alzheimer's type. In one specific aspect, the present invention is directed to an improved process for the isolation and purification of a ginsenoside useful in practicing that method.

BACKGROUND OF THE INVENTION

Senile dementia of the Alzheimer's type (SDAT) is widely recognized as a problem of increasing proportions in North America as well as around the world. The disease is associated with progressive physical and mental impairment to the point where the patient requires total care, and becomes a tremendous social and economic burden. Progress of the disease is believed to be related to degeneration of certain nerve tracts in the central nervous system, resulting in the loss of associated functions. Pathological studies indicate that brains of SDAT patients have loss of several neurotransmitter systems, related to different functions, but the system which is implicated the most is the cholinergic system. Studies show that several important cholinergic tracts innervating the cortical and hippocampal regions degenerate. Although this particular degeneration may not account for all of the symptoms of SDAT, it may account for the cognitive and memory deficits, which are some of the most difficult symptoms for patients and their families to deal with.

The pharmacological approaches which have been proposed for the managements of SDAT symptoms may be classified in two ways. The first is drugs which improve the function of existing neurons, especially to increase cholinergic nerve function. The second is drugs which decrease degeneration/increase regeneration of nerves.

Two types of drugs have been used in clinical trials to improve central cholinergic functions. The first is compounds which increase the availability of the existing endogenous neurotransmitter, acetylcholine (ACh); and the second is compounds which are exogenous, and mimic the effects of the endogenous transmitter at the receptor. However, these compounds exhibit side effects which limit their use.

It is generally believed that compounds which will increase the availability of the endogenous neurotransmitter are more desirable. Substances in this category are cholinesterase inhibitors, such as physostigmine and pyridostigmine, which decrease the breakdown of ACh, thus prolonging its functional lifetime at the crucial location, the synaptic cleft, and choline and lecithin, which increase the availability of the precursor for synthesis. Thus far, other compounds have not been described which directly increase the availability of the endogenous neurotransmitter ACh by any other mechanisms, except by blockade of inhibitory presynaptic receptors (with e.g. atropine or clonidine), or by non-specific depolarization of nerves (e.g. veratridine).

Ginseng is the name given to the dried roots of the ginseng plants (genus Panax) and, more particularly, to extracts of those roots. The roots and their extracts contain a variety of substances including saponins and sapogenins.

Ginseng has been extensively used, mostly in Asia, as a tonic to promote health and well being, and as a medicine in the treatment of various disease conditions. The beneficial attributes of ginseng are attributed to its saponin content, a mixture of glucosides referred to collectively as gensenosides.

DISCUSSION OF THE PRIOR ART

U.S. Pat. No. 4,157,894 to Bombardelli discloses the isolation of saponins from ginseng roots and the use of a purified concentrate in the geriatric field for elderly patients having difficulty in digesting less concentrated preparations. Bombardelli also discloses the structures of saponins $Rb_1$, $Rb_2$, Rc, Rd, Re, Rf and Rg.

U.S. Pat. No. 4,702,949 to Liu discloses a composition comprising 5–15% ginsenoside, 30–50% tetramethylpyrazine, 30–50% astragalan, and 5–15% atractylol in the treatment of cerebral vascular insufficiency and resultant paraplegia, hemiplegia and impaired neurofunction.

U.S. Pat. Nos. 4,157,894; 4,317,816; 4,446,130; 4,647,460; 4,684,628; 4,687,761; and 4,755,504 disclose the use of ginseng or ginseng extracts, alone, or in combination with other substances for various medically related purposes.

A procedure for the isolation of a crude mixture of ginsenosides from ginseng is described by J. Shoji, "Advances in Chinese Medicinal Materials Research", World Scientific Publishing Company, Singapore, pages 455–469 (1985). Material prepared by this established procedure is commercially available.

The preparation of ginseng extract s is also disclosed by Bombardelli and by Liu, discussed above, and in the other U.S. patents listed above. $Rb_1$ and $Rg_1$ have the structural formula:

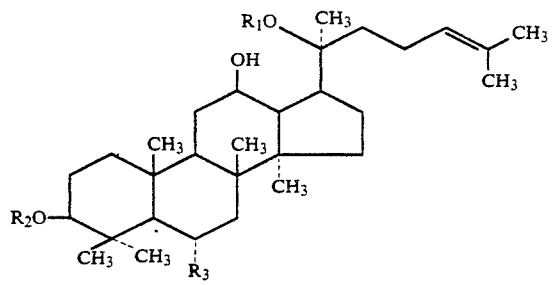

In $Rb_1$, $R_1$ is D-glucose $B(1\rightarrow6)$D-glucose, $R_2$ is D-glucose $B(1\rightarrow2)$D-glucose and $R_3$ is H. In $Rg_1$, $R_1$ is D-glucose, $R_2$ is H, and $R_3$ is O-D-glucose.

Existing procedures for the isolation and purification of ginsenoside $Rb_1$ include standard column chromatography, thin-layer chromatography, and high performance chromatography. These methods are laborious for the isolation of the compound in large quantities and often yield a low purity product.

BRIEF DESCRIPTION OF THE INVENTION

A primary object of the present invention is to provide compositions and methods for the treatment of senile dementia of the Alzheimer's type.

Another object of the invention is to provide an improved process for the isolation and purification of a ginsenoside used in that method for treating senile dementia.

We have discovered that ginsenosides $Rb_1$ and $Rg_1$ directly and selectively increase acetylcholine function in the brain and, accordingly, are useful in alleviating the symptoms of senile dementia. Those ginsenosides may be administered together with metabolic precursors for ACh synthesis and/or with cholinesterase inhibitors.

In one specific aspect, the present invention is a method for alleviating the symptoms of Alzeimer-type senile dementia, which comprises administering to a mammal affected with Alzheimer-type senile dementia an amount of ginsenoside $Rb_1$ or of ginsenoside $Rg_1$ effective to increase the availability of acetylcholine in the cortical and hippocampal regions in the brain of the mammal.

In a second specific aspect, the present invention is a process for the isolation of ginsenoside $Rb_1$ which comprises the steps:
 (a) dissolving a mixture of ginsenosides in methyl alcohol;
 (b) adsorbing the mixture of ginsenosides on silica gel by containing the solution of the mixture in methyl alcohol with the silica gel and evaporating the alcohol;
 (c) placing the silica gel having the mixture of ginsenosides adsorbed thereon in a column for vacuum chromatography prepacked with silica gel;
 (d) passing a mixture of chloroform and methyl alcohol through the columns to elute ginsenoside $Rb_1$; and
 (e) recovering ginsenoside $Rb_1$ from the chloroform and methyl alcohol eluate.

A mixture of ginsenosides enriched in $Rb_1$ particularly useful as the starting material in the process of the present invention may be obtained by:
 (a) dissolving a mixture of crude ginsenosides obtained by extraction of ginseng in water;
 (b) washing the aqueous solution of mixed ginsenosides with ethyl acetate;
 (c) extracting the ethyl acetate-washed solution successively with a mixture of 4 volumes of ethyl acetate and 1 volume of 1-butanol, with 1 volume of ethyl acetate and 1 volume of 1-butanol, and with 1-butanol pre-saturated with water;
 (d) combining the ethyl acetate-1-butanol and 1-butanol-water extracts; and
 (e) recovering a mixture of ginsenosides enriched in Rb1 from the combined extracts.

The vacuum chromatographic process described above yields ginsenoside $Rb_1$ of good quality and can be adapted to the preparation of larger amounts of that ginsenoside. Exceptionally high purity $Rb_1$ can be obtained by using a mixture of ginsenosides enriched in $Rb_1$ as the starting material in the process.

In a third specific aspect, the preset invention is a composition for alleviating the symptoms of Alzheimer-type senile dementia comprising:
 a) 25-250 mg of $Rb_1$ or $Rg_2$ together with a pharmaceutically acceptable carrier therefore,
 b) 25-250 mg of $Rb_1$ or $Rg_2$ and a metabolic precursor for acetylcholine, or
 c) 25-250 mg of $Rb_1$ or $Rg_2$ and a cholinesterase inhibitor.

BRIEF DESCRIPTION OF THE DRAWINGS

FIGS. 4 and 5 are a graphs of choline uptake plotted against log concentration $Rb_1$ and against log concentration $Rg_1$, respectively.

FIG. 6 is a graph of $^{45}Ca$ uptake at high and low concentrations of potassium.

DETAILED DESCRIPTION OF THE INVENTION

Our invention is further illustrated by means of the following non-limiting examples:

EXAMPLE 1

Isolation of $Rb_1$

About 1 g of crude ginsenosides obtained by the procedure described by Shoji in "Advances in Chinese Medicinal Materials Research" was dissolved in 10 ml of methanol. The resultant solution was mixed with 10 g of silica gel (Merck 0.040–0.063 mm particle size, 230–400 mesh ASTM). The silica gel was air dried for about 1 hour and then placed in a column for vacuum chromatography, as described by Coll et al, Aust. J. Chem., 30, 1305 (1977), prepacked with 80 g of silica gel. Elution with a solution of chloroform and methanol (85:15) gave a fraction from which 75mg of >98% pure $Rb_1$ was obtained. An additional 120 mg of $Rb_1$, purity about 60%, was recovered from other fractions of the eluate.

EXAMPLE 2

Preparation of Ginsenosides Enriched in $Rb_1$ 600 mg of the crude mixture of ginsenosides obtained by the procedure of Shoji was dissolved in 10 ml water. The aqueous solution was washed with ethyl acetate (2×40 ml) and then extracted with a solution of ethyl acetate and 1-butanol (4:1; 4 ×40 ml) followed by extraction with a 1:1 solution of ethyl acetate-1-butanol (2×40 ml) and then 1-butanol presaturated with water (2×40 ml). The last three extracts were combined and concentrated to give 140 mg of ginsenosides containing about 60% of $Rb_1$. Use of that enriched mixture as the starting material in Example 1 gave essentially pure $Rb_1$.

The following examples illustrate that $Rb_1$ and $Rg_1$ directly and selectively increase acetylcholine function in the brain and are useful in the treatment of Alzheimer-type senile dementia.

EXAMPLE 3

Figure 1:
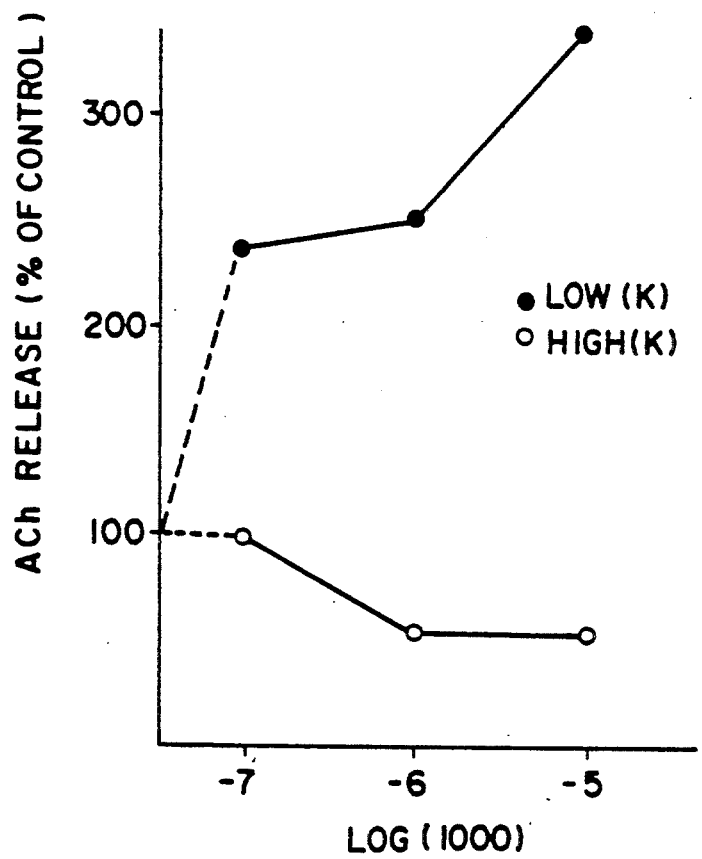
FIG. 1 is a graph of acetylcholine release plotted against log concentration $Rb_1$ at high and low concentrations of potassium.

Pinched off nerve endings (synaptosomes) from whole rat brain were first incubated in the presence of the precursor $^3$H-choline, which is converted intracellularly to $^3$H-ACh. The release of ACh from synaptosomes was quantitated under low [K] and high [K] conditions intended to simulate physiological stimulation. The addition of $Rb_1$ increased the release of $^3$H-ACh as shown in FIG. 1.

EXAMPLE 4

Figure 2B:
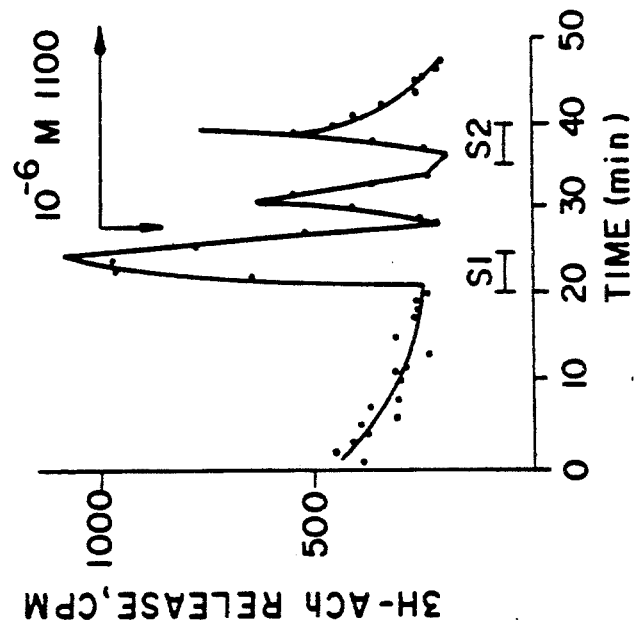
FIGS. 2A, 2B, 3A and 3B are graphs plotting electrically stimulated $^3H$-acetylcholine release against time.
Figure 2A:
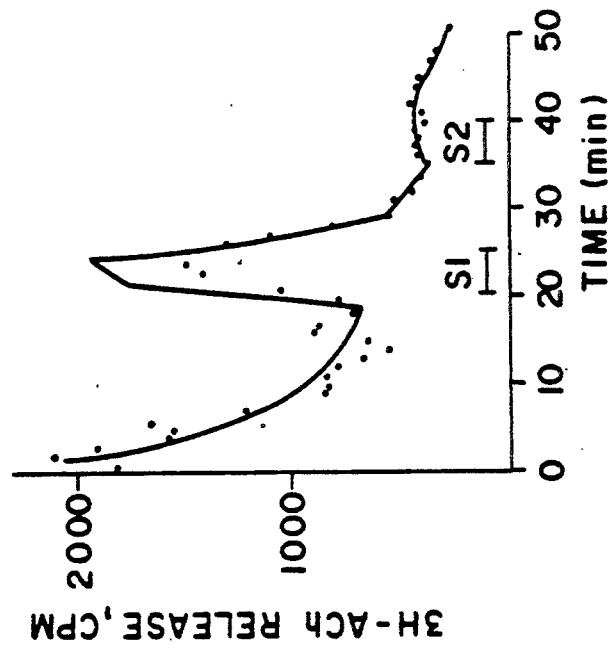
Figure 3B:
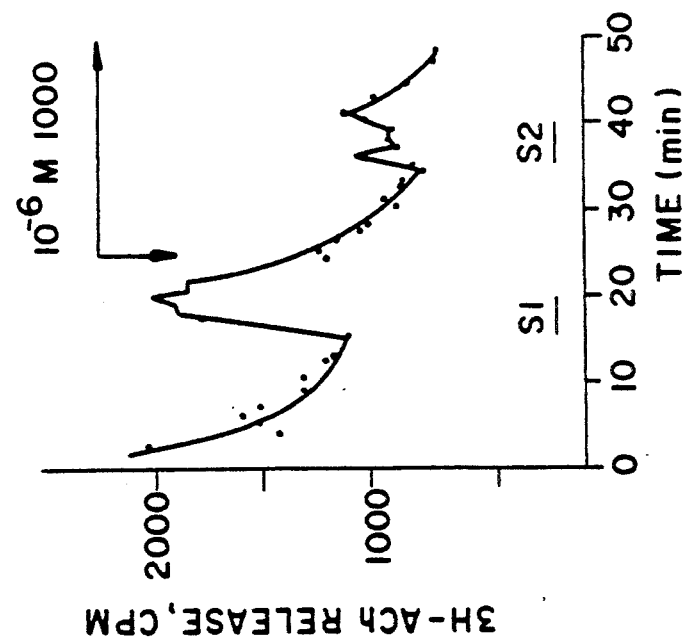
Figure 3A:
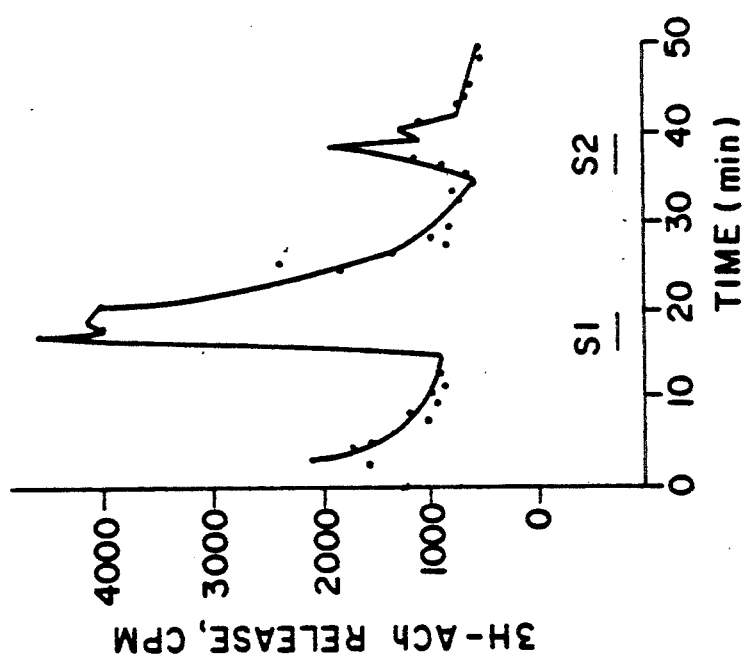

Using a different protocol, synaptosomes, which had been previously incubated with $^3$H-choline, as in the first series of experiments, were continually perfused with HEPES-buffered Krebs solution. The release of ACh was effected by subjecting the synaptosomes to electrical field stimulation, which more closely mimics physiological stimulation. In FIG. 2 and 3, the left panel shows the release pattern in the absence of any added drug, and the right panel shows the release pattern in the presence of $10^{-6}$ M drug during the last 25 minutes of perfusion. The results obtained by calculating the ratio of the amounts of ACh released during the two periods of electrical stimulation (the areas under the curves, S2/S1) indicate that both $Rb_1$ and $Rg_1$ increase the electrically stimulated release. In addition, $Rg_1$ stimulates the resting release of $^3$H-ACh, as indicated, by the increase in the resting afflux of $^3$H-ACh when the drug was first added. While the net amount of $^3$H-ACh released in each run can vary, depending on the amount of protein on the filter and aging of the synaptosomes, the S2/S1 ratio remains quite constant from run to run using a given chamber. Therefore, in each experiment the same chamber was used for both control and test-drug runs.

The stimulation of ACh release is also associated with an increase in the specific uptake of the precursor $^3$H choline as shown in FIGS. 4 and 5. Although the magnitude of stimulation of choline uptake is not as great as the magnitude of stimulation of ACh release, it is a consistent and significant effect, and can still quantitatively account for the increase in release. This suggests a general stimulation of brain cholinergic function. Further, preliminary experiments show that of three cholinergic brain regions examined, cortex, stratum, and hippocampus, stimulation of ACh release from synaptosomes is most pronounced in the hippocampus, a brain region strongly implicated in memory functions, and to a lesser extent in the cortex.

EXAMPLE 5

This example confirms that $Rb_1$ and $Rg_1$ do not stimulate the release of neurotransmitter by non-selectively depolarizing nerve endings. The effects of $Rb_1$ on the resting voltage dependent uptake of $^{45}$Ca into rat brain synaptosomes are shown in FIG. 6. these results indicate that the dramatic stimulation of $^3$H-ACh release is associated with only a minimal increase in the resting uptake of Ca, upon which ACh release is dependent. If this compound were acting as a non-specific depolarizing agent, one would predict the resting uptake of $^{45}$Ca would be stimulated several fold, to the same level as the depolarized (52.5 K) uptake.

EXAMPLE 6

Table 1 below contains data illustrating the effect of $Rb_1$ on the release of acetylcholine from hippocampal tissue, a brain region which is associated with memory and learning. These data indicate that $Rb_1$ can stimulate the release of ACh from brain tissue. This effect is observed in the presence or absence (10 mM EGTA) of calcium, which may suggest that the source of the stimulated release of ACh is not from the vesicular pool, as is normally the case, but from the cytoplasmic pool. Furthermore the stimulation of release in the absence of calcium is more pronounced in the simultaneous presence of a cholinesterase inhibitor, paraxon. This type of drug is also known to increase the amount of ACh in the cytoplasm, by virtue of its ability to inhibit intracellular AChE, and this observation would be consistent with the notion that the source of ACh which is stimulated by $Rb_1$ is the cytoplasm.

TABLE 1

| CONDITION | RATIO | N |
|---|---|---|
| with Paraoxon | | |
| Control | 1.053 ± 0.058 | 29 |
| 10 mM EGTA | 0.299 ± 0.062 | 10 |
| $10^{-7}$M $Rb_1$ | 2.107 ± 0.284 | 14 |
| $10^{-6}$M $Rb_1$ | 1.380 ± 0.112 | 10 |
| $10^{-6}$M $Rb_1$ + 10 mM EGTA | 1.139 ± 0.338 | 9 |
| without Paraoxon | | |
| Control | 1.022 ± 0.024 | 24 |
| 10 mM EGTA | 0.357 ± 0.126 | 6 |
| $10^{-7}$M $Rb_1$ | 2.108 ± 0.542 | 11 |
| $10^{-6}$M $Rb_1$ | 1.428 ± 0.169 | 10 |
| $10^{-6}$M $Rb_1$ + 10 mM EGTA | 0.676 ± 0.194 | 9 |

EXAMPLE 7

Figure 7:
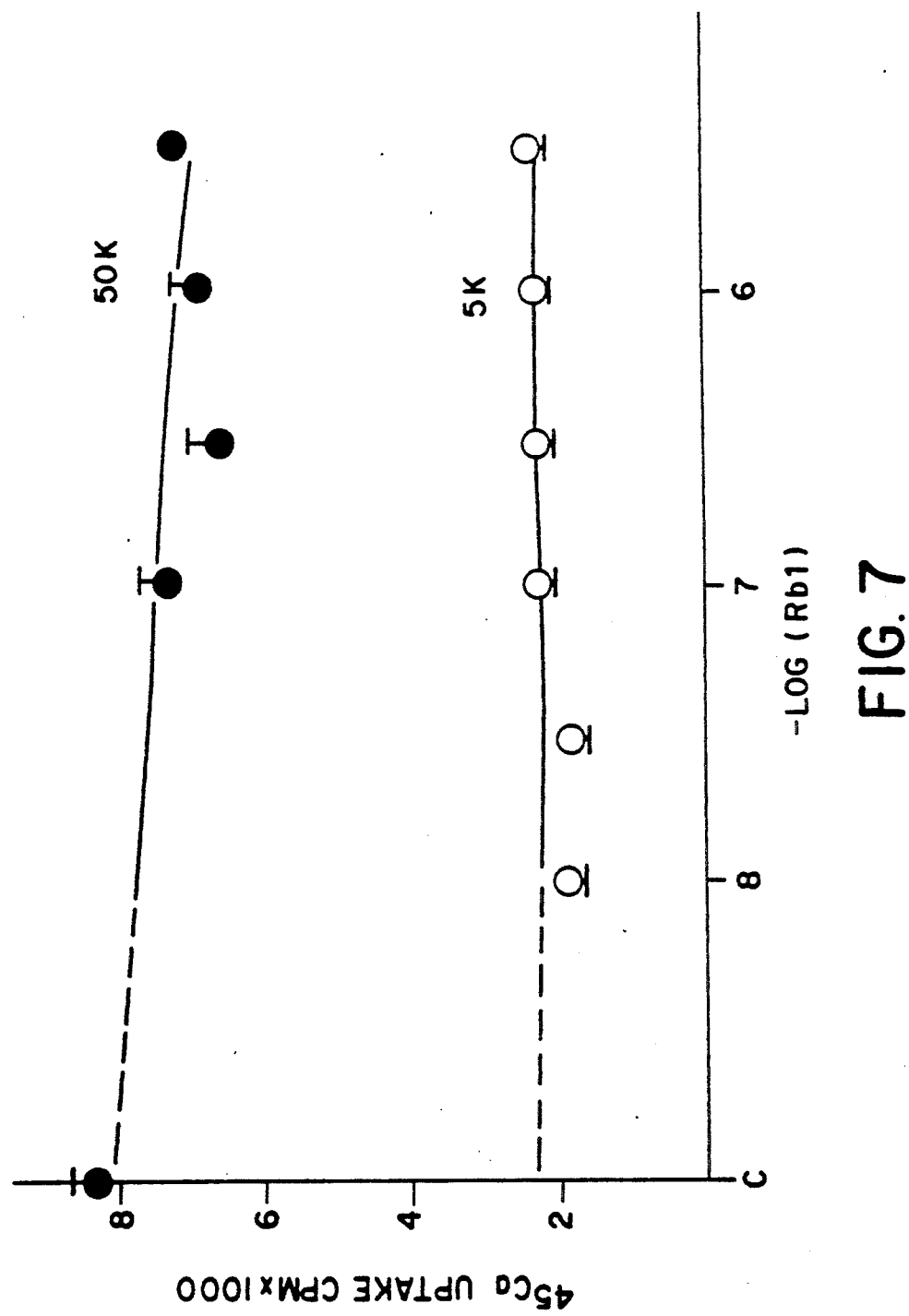
FIG. 7 is a graph showing the effects of $Rb_1$ on calcium uptake at nerve endings.
Figure 8:
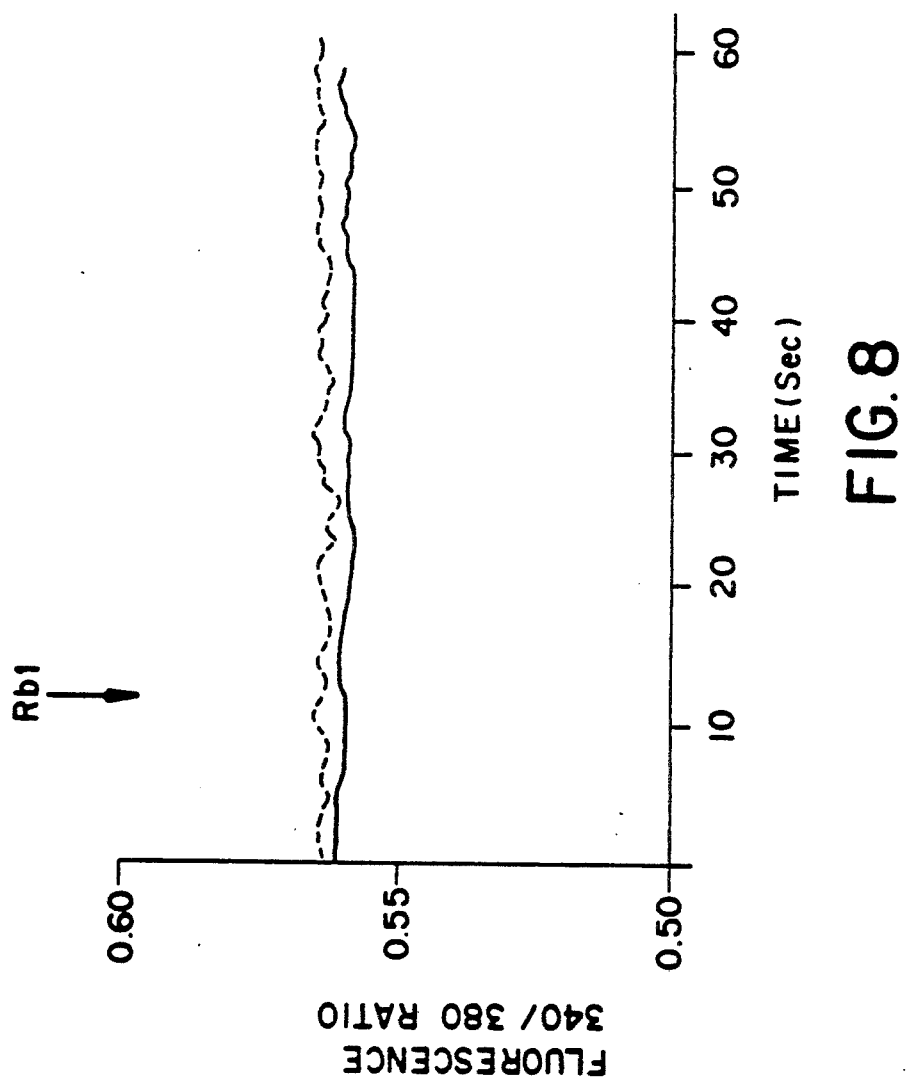
FIG. 8 is a graph showing the effects of $Rb_1$ on intracellular calcium concentration in cultured neuroblastoma cells.

The stimulation of ACh release is not accompanied by an increase in intracellular calcium in nerves. FIG. 7 shows the effects of $Rb_1$ on nerve ending calcium uptake, and FIG. 8 shows the effects of $Rb_1$ on the intracellular calcium concentration in cultured neuroblastoma cells.

EXAMPLE 8

Figure 9:
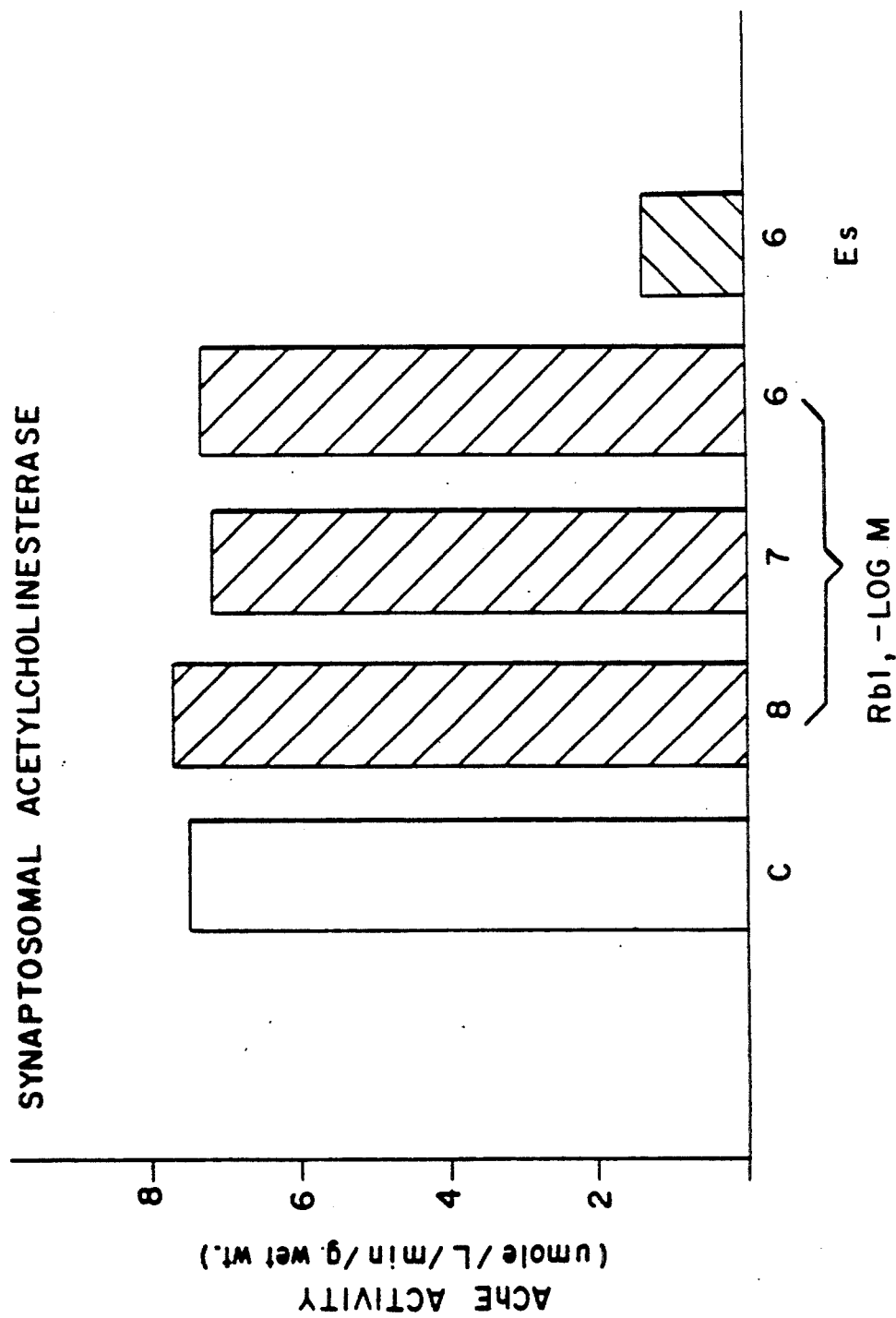
FIG. 9 is a graph illustrating that $Rb_1$ itself has no anticholinesterase (AChE) activity.

FIG. 9 shows that $Rb_1$ itself also has no anticholinesterase activity.

EXAMPLE 9

Table 2 below summarizes the effect of $Rb_1$ on the intracellular stores of choline and ACh when tissues are incubated in low or high potassium, and in the absence or presence of $Rb_1$. $Rb_1$ produces an increase in and in the absence or presence of $Rb_1$. $Rb_1$ produces an increase in the total $^3$H contents (choline and ACh) and in the ACh contents of the cytoplasmic fraction (S3), but not in the vesicular (P3) fraction.

TABLE 2

| | S3 | P3 |
|---|---|---|
| Total $^3$H contents of Subcellular Fractions | | |
| Low K | 166.3 ± 20.1 | 55.1 + 4.2 |
| Low K + $Rb_1$ | 214.4 ± 18.9 | 62.0 ± 5.5 |
| High K | 209.0 ± 19.5 | 87.3 ± 7.3 |
| High K + $Rb_1$ | 216.0 ± 21.8 | 97.2 ± 8.8 |
| $^3$H ACh Contents of Subcellular Fractions | | |

TABLE 2-continued

| | S3 | P3 |
|---|---|---|
| Low K | 38.6 ± 9.4 | 7.0 ± 0.72 |
| Low K + $Rb_1$ | 48.5 ± 6.9 | 7.8 ± 0.3 |
| High K | 16.8 ± 0.9 | 8.0 ± 0.9 |
| High K + $Rb_1$ | 17.8 ± 0.9 | 6.8 ± 0.7 |

EXAMPLE 10

Figure 10:
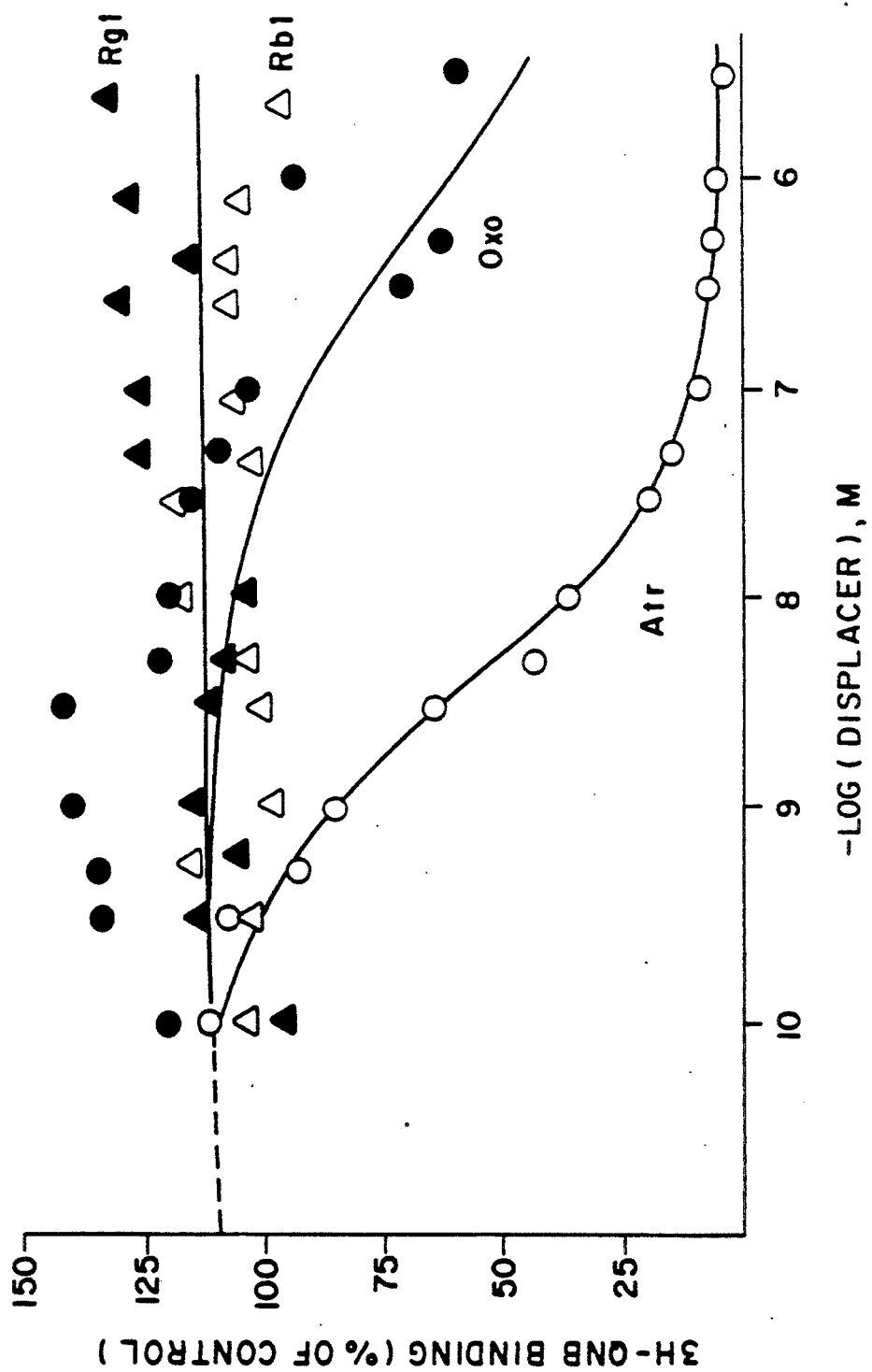
FIG. 10 is a graph showing the inability of $Rb_1$ to displace QNB from nerve ending receptors.

The stimulation in activity is not mediated by autoreceptors. FIG. 10 shows the lack of ability of $Rb_1$ to bind to nerve ending muscarinic receptors (displace QNB from its nerve ending receptor).

EXAMPLE 11

Figure 11:
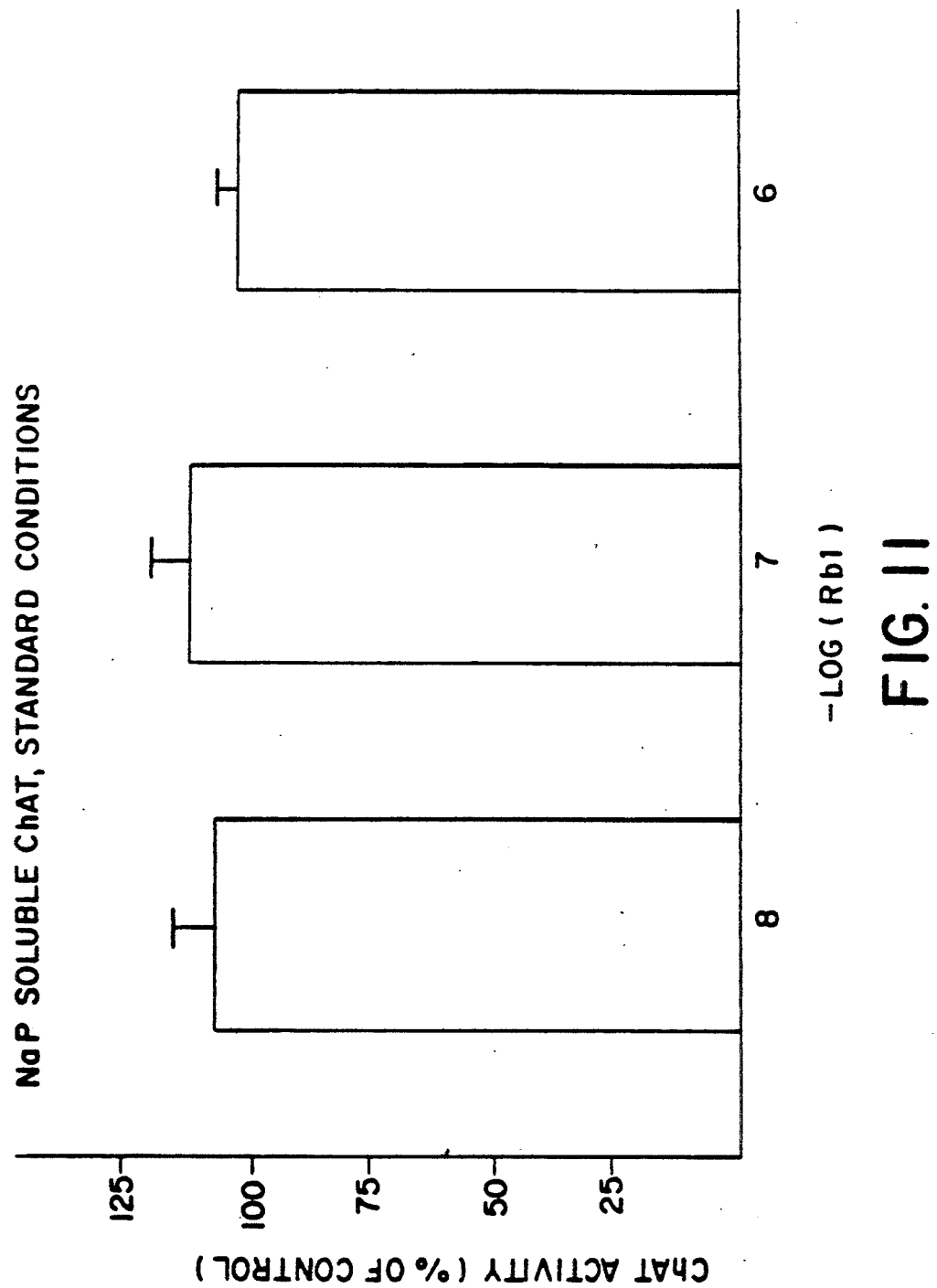
FIGS. 11 and 12 are graphs illustrating that the increase in ACh content at nerve endings is not caused by an increase in activity choline acetyltransferase (ChAT).
Figure 12:
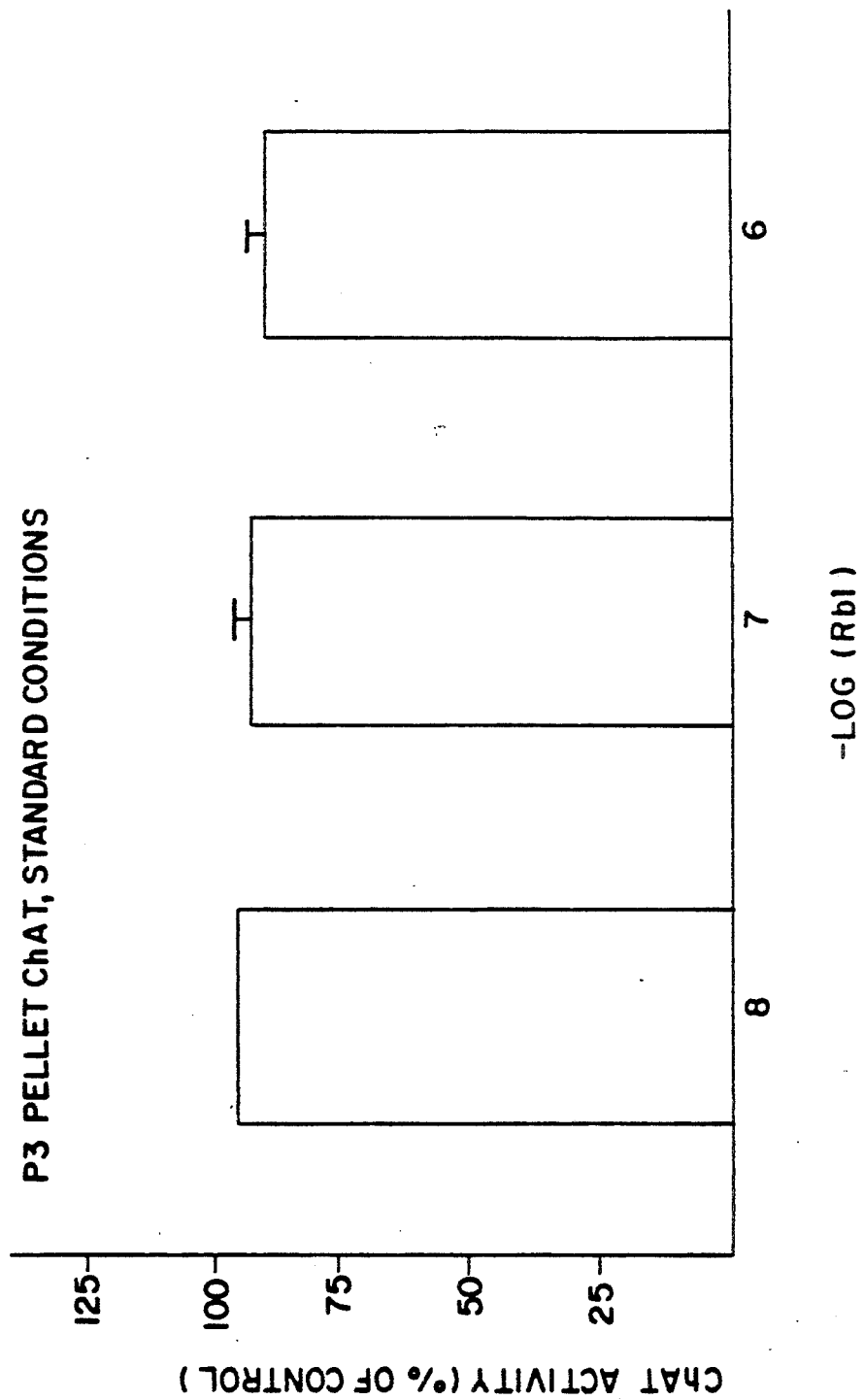

The increase in the nerve ending ACh content is not caused by an increase in the activity of the synthetic enzyme choline acetyltransferase (ChAT) as is shown in FIGS. 11 and 12.

EXAMPLE 12

Figure 13:
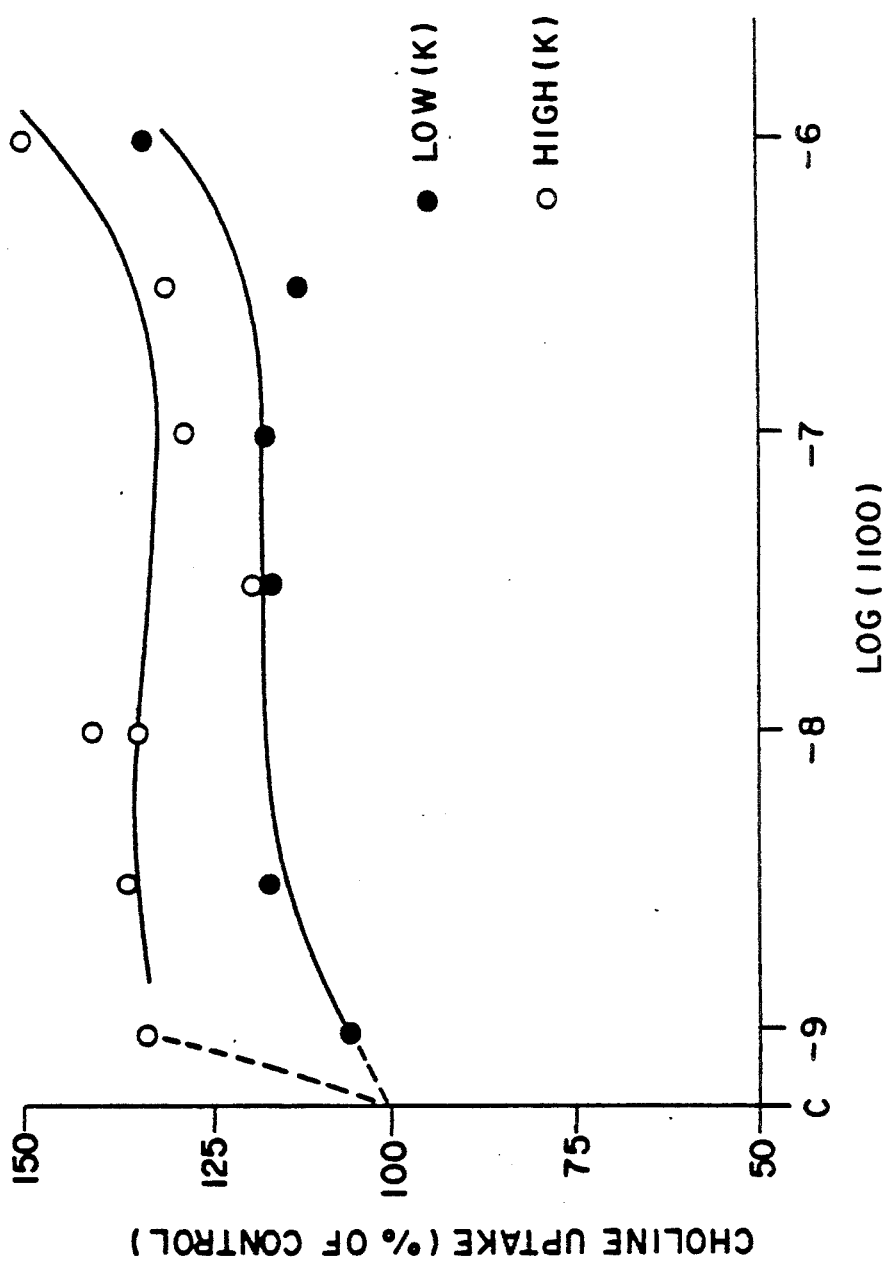
FIG. 13 is a graph illustrating that the increase in the release of ACh is accompanied by an increase in the uptake of choline into the nerve endings.
Figure 14:
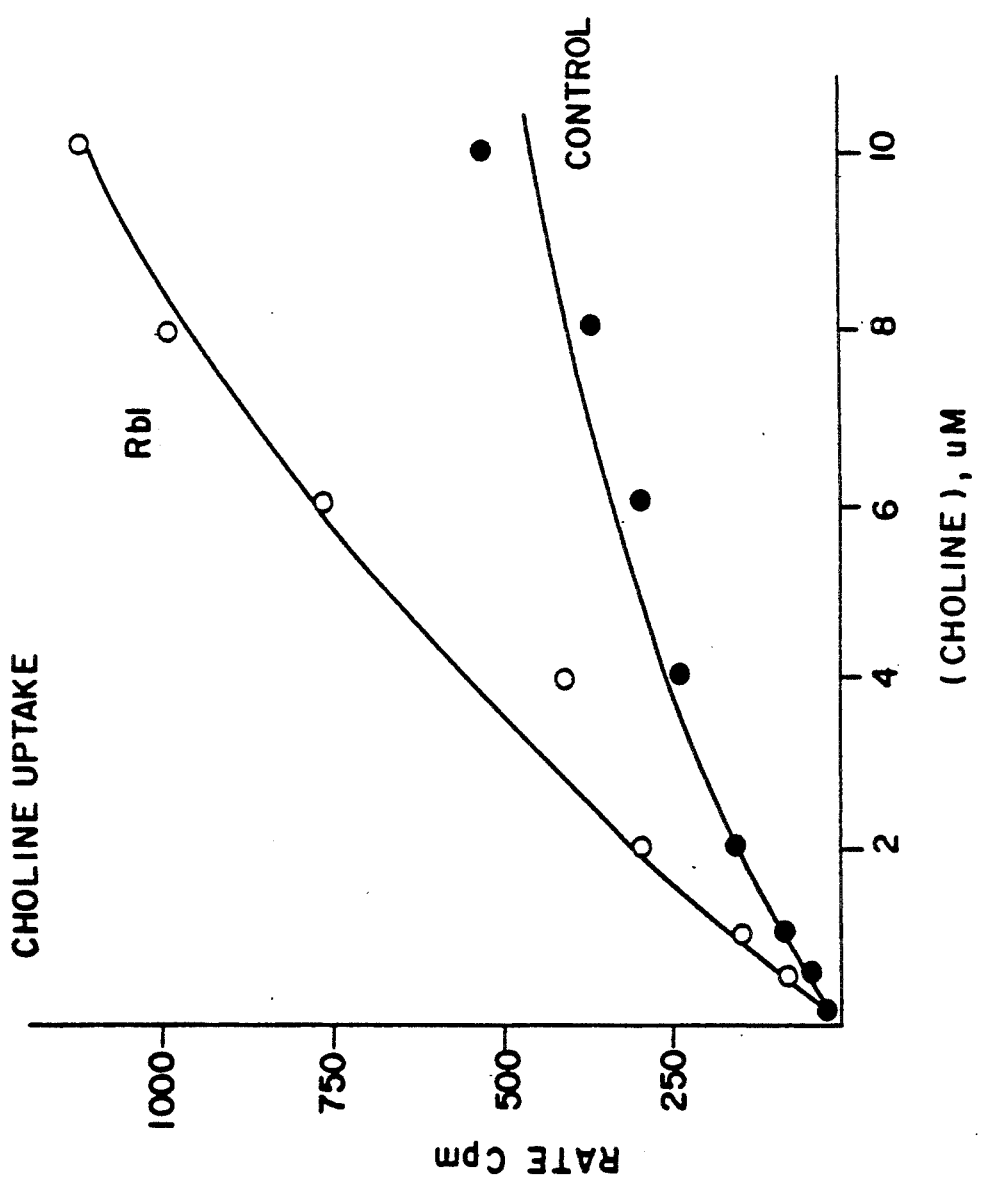
FIGS. 14 and 15 are graphs illustrating the kinetics of that uptake.
Figure 15:
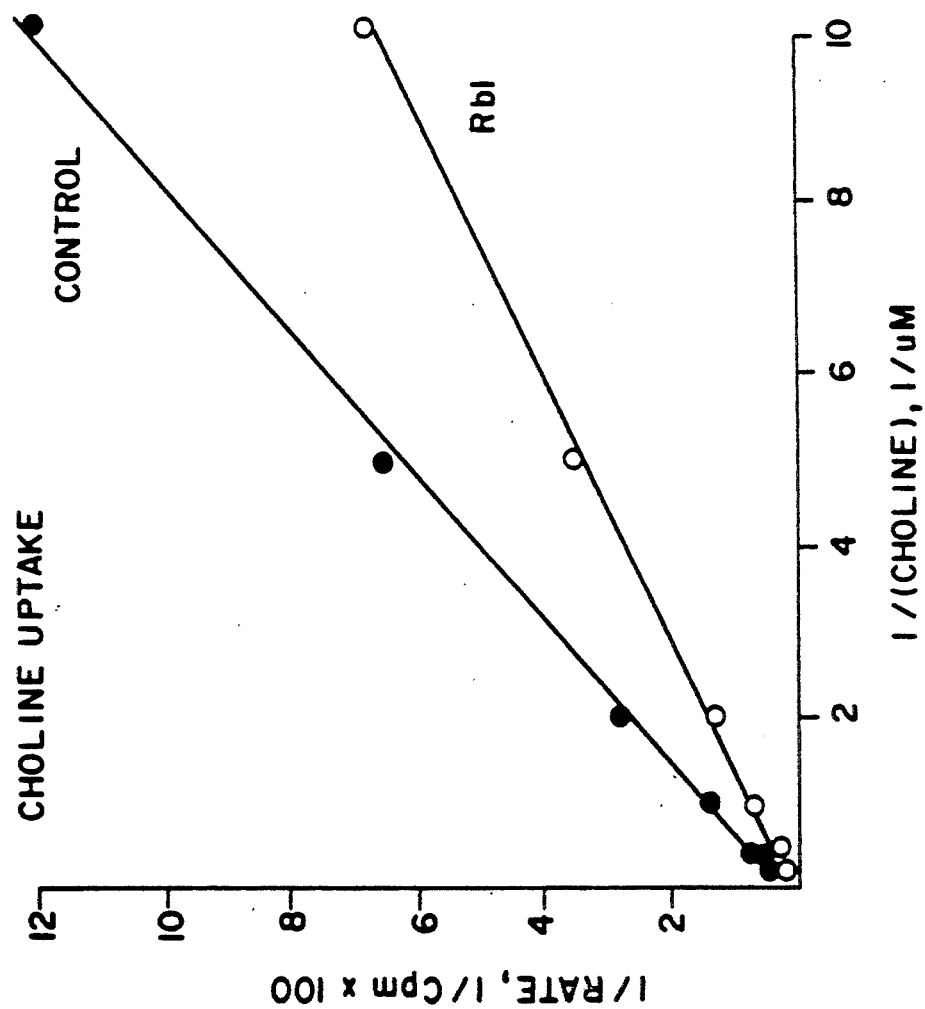

The increase in the release of ACh is accompanied by an increase in the uptake of the precursor choline into nerve endings, which is shown in FIG. 13. The kinetics of the increase in uptake are presented in FIGS. 14 and 15, and the kinetic contents are presented in Table 3. These results indicate that the increase in choline uptake is not due to an increase in the affinity of the carrier for the substrate choline, but to an increase in the maximum velocity of the carrier.

TABLE 3

| | Km | $v_{max}$ |
|---|---|---|
| Control | 12.74 μM | 475 |
| $10^{-10}$ $Rb_1$ | 6.037 μM | 709.4 |
| $10^{-8}$ $Rb_1$ | 31.1 μM | 4572 |

Figure 16:
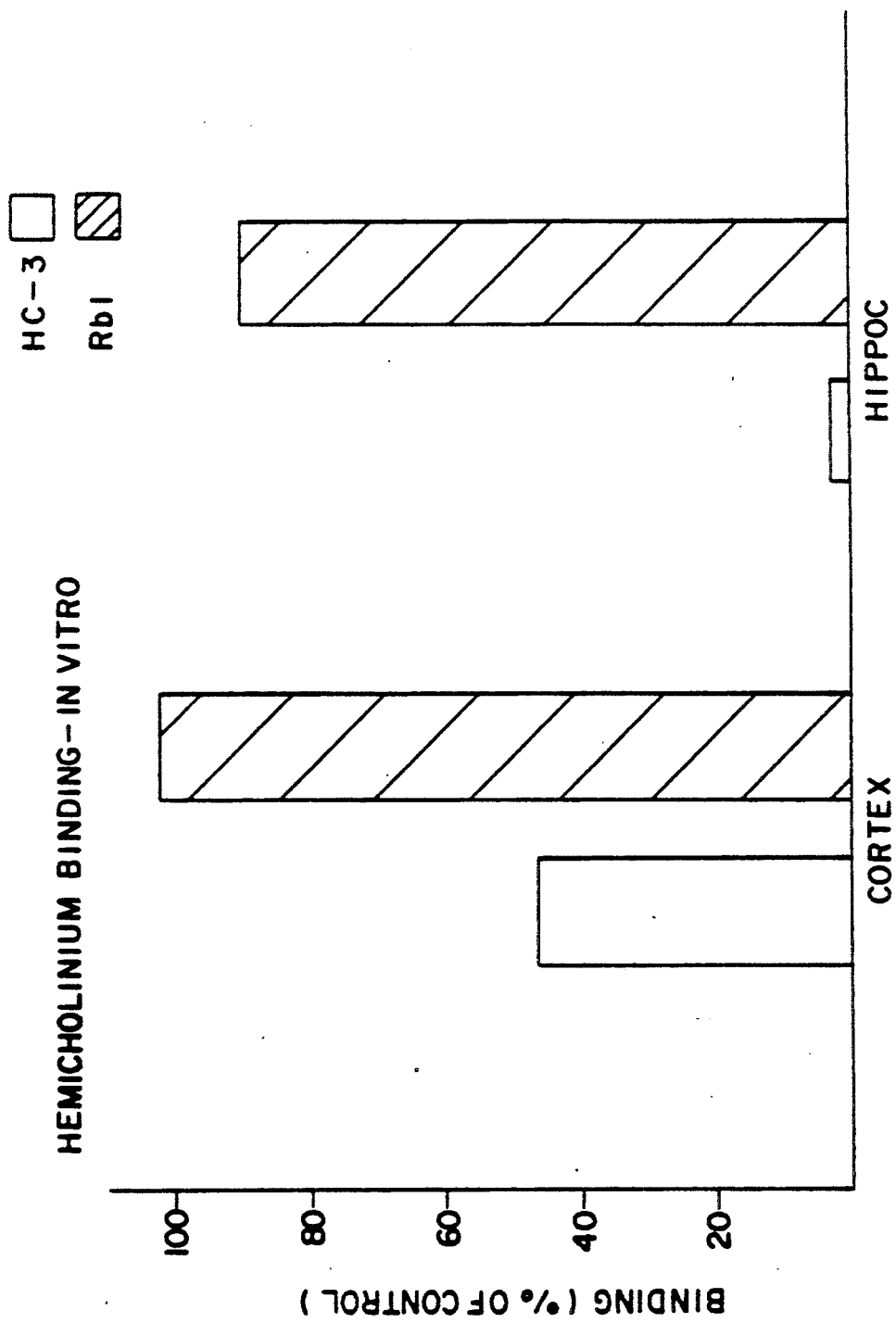
FIG. 16 is a graph illustrating that $Rb_1$ does not displace radio labelled HC-3 and did not increase the number binding sites in the brain.
Figure 17:
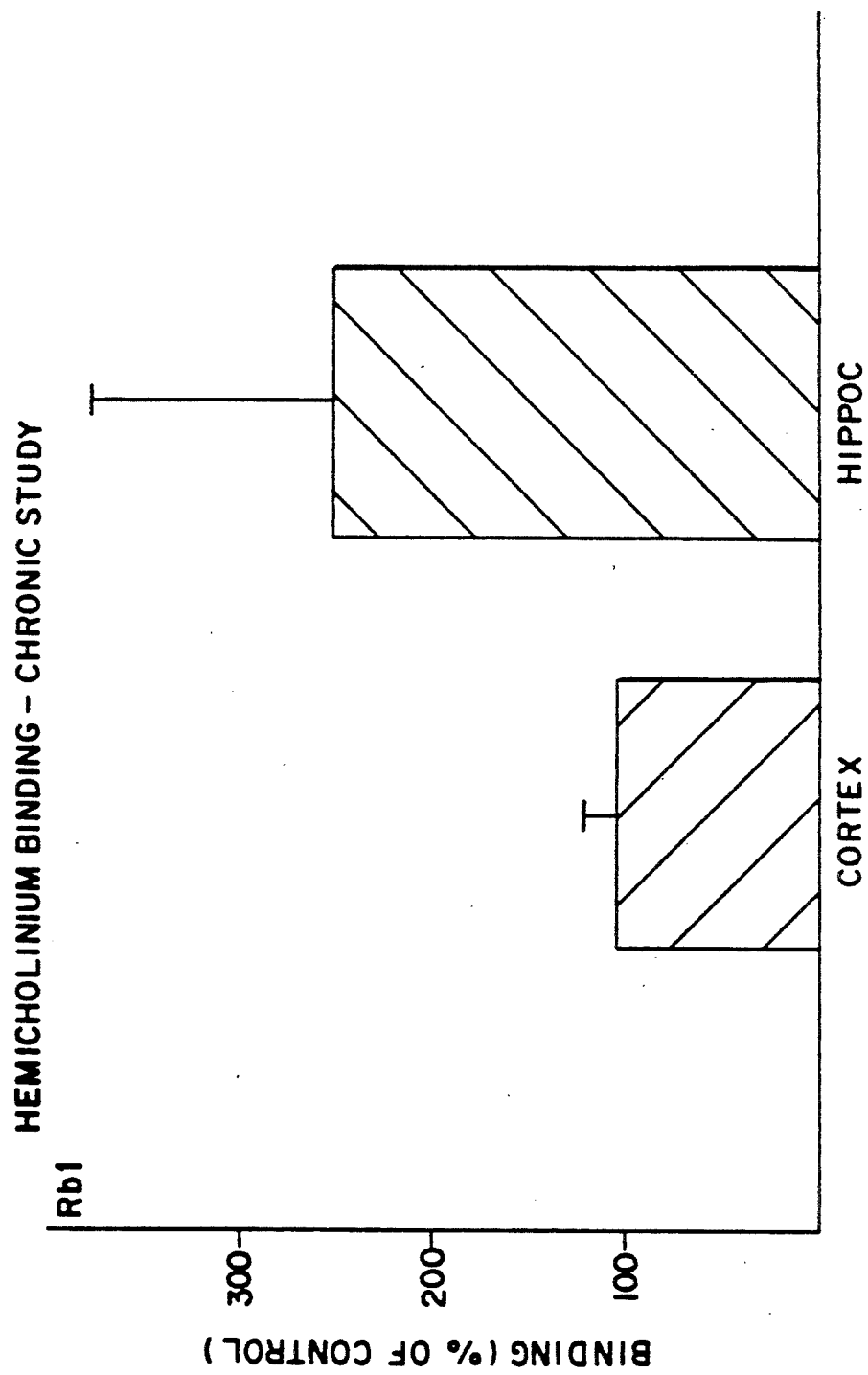
FIG. 17 is a graph illustrating that the administration of $Rb_1$, increases the number of choline-uptake sites in the rat.

The mechanism of the increase in the velocity of the carrier could be accounted for in two ways (1) an increase in the turnover rate of the carriers, or (2) in increase in the number of carriers in the plasma membrane. In order to discriminate between these two possibilities, the number of carrier sites was probed with radiolabelled hemicholinium-3 (HC-3). In in vitro administration experiments, presented in FIG. 16, $Rb_1$ did not displace radiolabelled HC-3 (unlabelled HC-3 was also used as a displacer, as a positive control), and did not increase the apparent number of binding sites. Initially, $Rb_1$ seems to increase the uptake of choline by simply increasing the turnover rate of the carriers. When rats were administered with $Rb_1$ (5mg/kg/day) for three days, there was an increase in the number of choline uptake sites, suggesting that chronic administration of the compound increases the number of carriers (FIG. 17).

When using $Rb_1$ and $Rg_1$ to alleviate the symptoms of Alzheimer-type senile dementia, $Rb_1$ and $Rg_1$ can be processed by conventional methods of galenic pharmacy into pharmaceutical preparations for oral or parenteral administration, e.g., to mammals including humans. Conventional excipients are pharmaceutically acceptable organic or inorganic carrier substances suitable for parenteral, enteral or topical application which do not deleterious react with $Rb_1$ or $Rg_1$. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with $Rb_1$ and $Rg_1$.

For parental application, particularly suitable are injectable sterile solutions, preferably oily or aqueous solutions, as well as suspensions, emulsions, or implants, including suppositories.

For enteral application, particularly suitable are tablets, dragees, suppositories or capsules having talc and-/or sa carbohydrate carrier or binder or the like, the carrier preferably being lactose and/or corn starch and/or potato starch.

A syrup, elixir or the like can be used wherein a sweetened vehicle is employed. Sustained release compositions can be formulated including those wherein Rb1 and Rg1 is protected with differential degradable coatings, e.g., by microencapsulation, multiple coatings, etc.

Depending on the type of mammal to which it is being administered, the daily dosage of $Rb_1$ or $Rg_1$ for a mammal weighing 50 kg is generally about 100–1000 mg. preferably administered 3 or 4 times a day in divided doses. Thus, a suitable dosage form would contain 25–250 mg of $Rb_1$ or $Rg_1$. Suitable daily dosages of metabolic precursors of acetylcholine, and of cholinesterase inhibitors, are well known to those skilled in the art. For example, acetylcholine precursor, such as choline, usually as its chloride or bitartrate, dimethylaminoethanol, a synthetic precursor of choline, phosphatidylcholine and lecithin, are generally administered in amounts ranging from 5 to 50 g/day. Choline and lecithin are sometimes administered in conjunction with nootropic agents such as piracetam, amalogues of piracetam and aminopyridines. As for acetylcholinesterase inhibitors, the usual dose for neostigmine is 15–30 mg, for pyridostigmine 60–180 mg, for ambenonium 10–20 mg, and for tetrahydroacridine 25–150 mg. When $Rb_1$ or $Rg_1$ is administered together with a metabolic precursor acetylcholine and/or a cholinesterase inhibitor, the dosage form will generally contain the usual dosage of the acetylcholine precursor and/or the usual dosage of the cholinesterase inhibitor. Appropriate dosages and regimens for a given host can be determined using conventional considerations, e.g., by customary comparison of the differential activities of the subject compound and of a known agent, e.g., by means of conventional pharmacological protocols.

What is claimed is:

1. A method for alleviating the symptoms of Alzheimer type senile dementia, which comprises administering to a mammal affected with Alzheimer-type senile dementia an amount of ginsenoside $Rb_1$ or of ginsenoside $Rg_1$, effective to increase the availability of acetylcholine in the cortical and hippocampal regions in the brain of the mammal.

2. A method according to claim 1, wherein the $Rb_1$ or $Rg_1$, is administered to the mammal in a daily dosage of 100–1000 mg.

3. A method according to claim 2, wherein the daily dosage is administered in portions 3 or 4 times per day.

4. A method according to claim 1, wherein the Rb₁ or Rg₁, is administered together with a metabolic precursor for acetylcholine.

5. A method according to claim 4, wherein the metabolic precursor is lecithin or choline.

6. A method according to claim 1, wherein the Rb₁ or Rg₁, is administered together with a cholinesterase inhibitor.

7. A method according to claim 6, wherein the cholinesterase inhibitor is physostigmine, pyridostigmine or paraoxon.

8. A method according to claim 1, wherein the Rb₁ or Rg₁ is administered together with a metabolic precursor for acetycholine and an acetylcholinesterase inhibitor.

9. A composition for alleviating the symptoms of Alzheimer-type senile dementia comprising 25-100 mg of Rb₁ or Rg₁ and a metabolic precursor for acetylcholine.

10. A composition for alleviating the symptoms of Alzheimer-type senile dementia comprising 25-100 mg of Rb₁ or Rg₁ and a cholinesterase inhibitor.

11. A composition for alleviating the symptoms of Alzheimer-type senile dementia comprising 25-100 mg of Rb₁ or Rg₁, a metabolic precursor for acetylcholine and a cholinesterase inhibitor.

* * * * *

UNITED STATES PATENT AND TRADEMARK OFFICE
CERTIFICATE OF CORRECTION

PATENT NO. : 5,137,878

DATED : August 11, 1992

INVENTOR(S) : Pang et al.

It is certified that error appears in the above-identified patent and that said Letters Patent is hereby corrected as shown below:

On the title page, Item [86]:
Please correct the PCT No. from "PCT/US90/00/21" to --PCT/US90/00121--; and change [63] Continuation-in- Part Serial No. from "297,021" to --297,012--.

Signed and Sealed this

Fourteenth Day of December, 1993

*Attest:*

BRUCE LEHMAN

*Attesting Officer*     *Commissioner of Patents and Trademarks*